United States Patent
Chang et al.

(10) Patent No.: US 9,140,839 B2
(45) Date of Patent: Sep. 22, 2015

(54) LIGHTING MODULE AND OPTICAL FIBER LIGHTING DEVICE USING THE SAME

(71) Applicants: INDUSTRIAL TECHNOLOGY RESEARCH INSTITUTE, Hsinchu (TW); KARL STORZ GmbH & Co. KG, Tuttlingen (DE)

(72) Inventors: Hsueh-Chih Chang, Changhua County (TW); Hung-Lieh Hu, Hsinchu (TW)

(73) Assignees: INDUSTRIAL TECHNOLOGY RESEARCH INSTITUTE, Hsinchu (TW); KARL STORZ GMBH & CO. KG, Tuttlingen (DE)

( * ) Notice: Subject to any disclaimer, the term of this patent is extended or adjusted under 35 U.S.C. 154(b) by 0 days.

(21) Appl. No.: 14/310,740

(22) Filed: Jun. 20, 2014

(65) Prior Publication Data

US 2015/0016142 A1 Jan. 15, 2015

Related U.S. Application Data

(60) Provisional application No. 61/846,116, filed on Jul. 15, 2013.

(51) Int. Cl.
*F21K 99/00* (2010.01)
*F21V 8/00* (2006.01)
*A61B 1/00* (2006.01)

(52) U.S. Cl.
CPC ............... *G02B 6/0005* (2013.01); *A61B 1/00* (2013.01); *G02B 6/0006* (2013.01)

(58) Field of Classification Search
CPC ............................ G02B 6/0006; G02B 6/0008
See application file for complete search history.

(56) References Cited

U.S. PATENT DOCUMENTS

| | | | |
|---|---|---|---|
| 7,356,054 B2 | 4/2008 | Hama et al. | |
| 7,494,228 B2 | 2/2009 | Harbers et al. | |
| 7,557,985 B2 | 7/2009 | Hama et al. | |
| 7,591,575 B2 | 9/2009 | Hama et al. | |
| 7,672,041 B2 | 3/2010 | Ito | |
| 7,758,224 B2 | 7/2010 | Hama et al. | |
| 7,780,326 B2 | 8/2010 | Ito | |
| 8,197,111 B2 | 6/2012 | Hama et al. | |
| 8,506,478 B2 | 8/2013 | Mizuyoshi | |
| 2011/0208004 A1 | 8/2011 | Feingold et al. | |
| 2012/0033403 A1* | 2/2012 | Lamvik et al. | 362/84 |
| 2012/0106189 A1* | 5/2012 | Takahashi et al. | 362/538 |

FOREIGN PATENT DOCUMENTS

| | | |
|---|---|---|
| CN | 101610708 A | 12/2009 |
| CN | 102679209 A | 9/2012 |

(Continued)

OTHER PUBLICATIONS

Thomas Weyh et al., "Developing a Fibre-Coupled LED Cold-Light Source" Medical Device Components, Dec. 9, 2010.

(Continued)

*Primary Examiner* — Thomas M Sember
(74) *Attorney, Agent, or Firm* — Rabin & Berdo, P.C.

(57) ABSTRACT

A lighting module comprises a first light source, a second light source and a phosphor element is provided. The first light source emits a first exciting light. The second light source emits a second exciting light. The phosphor element converts the first exciting light and the second exciting light to an emission light. The first exciting light and the second exciting light are input to the phosphor element in different directions of incidence.

15 Claims, 6 Drawing Sheets

(56) References Cited

FOREIGN PATENT DOCUMENTS

| DE | 102010013835 A1 | 9/2011 |
| TW | 201326683 A | 7/2013 |
| WO | WO-2012116733 A1 | 9/2012 |

OTHER PUBLICATIONS

Kevin Rogers et al., "An Investigation into LED Multiplexing and Homogenisation" Photonics West 2011, SPIE paper 7933-41, Jan. 2011.

Benjamin A. Jacobson et al., "Metal Halide Lighting Systems and Optics for High Efficiency Compact LCD Projectors" Part of the IS&T/SPIE Conference on Projection Displays IV, SPIE vol. 3296, Jan. 1998.

Matthew S. Brennesholtz "Light Collection Efficiency for Light Valve Projection Systems" SPIE 2650, Project Displays II, Mar. 1996.

Harold Ries et al., "Performance limitations of rotationally symmetric nonimaging devices" J. Opt. Soc. Am. A vol. 14, Issue 10, pp. 2855-2862, Oct. 1997.

James Larimer, "A Laser Light Source for Endoscopy" Versatile Power 2010, Version 3.1, Jan. 2010.

* cited by examiner

LIGHTING MODULE AND OPTICAL FIBER LIGHTING DEVICE USING THE SAME

This application claims the benefit of U.S. provisional application Ser. No. 61/846,116, filed Jul. 15, 2013, the disclosure of which is incorporated by reference herein in its entirety.

TECHNICAL FIELD

The disclosure relates in general to a lighting module, and more particularly to an optical fiber lighting device using that lighting module.

BACKGROUND

For many lighting device utilizing optical fiber, in particular for endoscopy, microscopy and medical headlamps, lighting module with high lumen output as well as high brightness are necessary. Traditionally, Xenon short-arc discharge lamps with power input of several 100 W, embedded in optical reflectors, have been used. Due to the relatively high input power, limited lifetime with shifting luminous properties and adverse thermal impact on illuminated targets, there has been growing demand for alternative, more energy efficient light sources.

SUMMARY

The disclosure is directed to a lighting module and an optical fiber lighting device using the same. The lighting module includes two light sources and can provide sufficiently bright illumination light inputting optical fiber.

According to one embodiment, a lighting module is provided. The lighting module comprises a first light source, a second light source and a phosphor element. The first light source emits a first exciting light. The second light source emits a second exciting light. The phosphor element converts the first exciting light and the second exciting light to an emission light. The first exciting light and the second exciting light are input to the phosphor element in different directions of incidence.

According to another embodiment, an optical fiber lighting device is provided. The optical fiber lighting device comprises a first light source, a second light source, a phosphor element, an optical fiber and a mixing chamber. The first light source emits a first exciting light. The second light source emits a second exciting light. The phosphor element converts the first exciting light and the second exciting light to an emission light. The first exciting light and the second exciting light are input to the phosphor element in different directions of incidence. The optical fiber is disposed above the phosphor element and receives the first exciting light, the second exciting light and the emission light. The mixing chamber is disposed between the optical fiber and the phosphor element and is for mixing and guiding the first exciting light, the second exciting light and the emission light.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

First Embodiment

Figure 1:
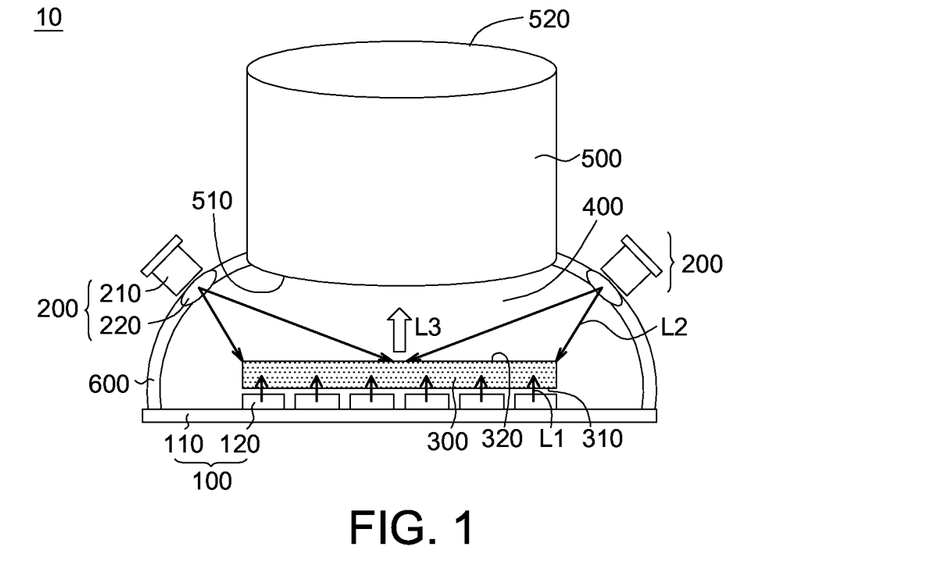
FIG. 1 shows an optical fiber lighting device according to a first embodiment.

Referring to FIG. 1, an optical fiber lighting device 10 according to a first embodiment is disclosed. The optical fiber lighting device 10 comprises a first light source 100, a second light source 200, a phosphor element 300, a mixture chamber 400 and an optical fiber 500. The first light source 100 emits a first exciting light L1. The second light source 200 emits a second exciting light L2. The phosphor element 300 can convert the first exciting light L1 and the second exciting light L2 to an emission light L3. The remaining portion of the first and second exciting light L1, L2 and the emission light L3 are mixed in the mixing chamber 400, being guided to an entrance 510 of the optical fiber 500 and thus emit from the exit 520 of the optical fiber 500.

As shown in FIG. 1, the first light source 100 and the second light source 200 are disposed at opposite sides of the phosphor element 300. The first light source 100 is disposed below the phosphor element 300, and the second light source 200 are disposed above the phosphor element 300. The first light source 100 and the second light source 200 can be the same or different. For example, the first light source 100 and the second light source 200 can be cold light such as LED (light emitting diode) or LD (laser diode). Comparing to traditional hot light Xenon lamp, the LED and LD have lower input power and heat release, longer lifetime and can be easily dimmer by PWM or other technique. In present embodiment, the first light source is a LED array including a substrate 110 and a plurality of LEDs 120, wherein the LEDs 120 are disposed on the substrate 110 at a pitch. The second light source 200 in present embodiment is two LD units, each includes a LD 210. LD210 may be combined with a lens 220 for adjusting the divergent angle of the LD 210. The number of the LD units are not limited there to. In some embodiments, the second light source 200 could be only one LD unit or more than 3 LD units.

As shown in FIG. 1, the phosphor element 300 is disposed between the first light source 100 and the second light source 200. The phosphor element 300 includes different types of phosphors, which are mixed with a resin, and the bottom surface 310 of the phosphor element 300 is attached the first light source 100. In other embodiment, the phosphor element 300 and the first light source 100 can be spaced apart at an interval. The phosphor element 300 emits different types of fluorescences in accordance with the reception of the first exciting light L1 and the second exciting light L2. These types of fluorescences combine to become an emission light L3-. Emission light L3 may combine the remain portion of the first exciting light L1 and the second exciting light L2 to become the white light. In present embodiment, the first exciting light L1 and the second exciting light L2 input to the phosphor element 300 through different directions of incidence. That is, the first exciting light L1 inputs the phosphor element 300 through its bottom surface 310, and the second exciting light L2 inputs the phosphor element 300 through its top surface 320. Thus, the phosphors inside the phosphor element 300 can receive more exciting light before it reaching saturated absorption, thereby improving the illuminance of the emission light L3.

As shown in FIG. 1, the mixing chamber 400 is a region located between the phosphor element 300 and the optical fiber 500. Generally, the phosphor element 300 is hard to convert all the first exciting light L1 and all the second exciting light L2 to the emission light L3. The remaining portion of the first exciting light L1, the remaining portion of the second exciting light L2 and the emission light L3 are mixing at the mixing chamber 400 and then guided to the entrance 510 of optical fiber 500. The mixing chamber 400 can be defined by the frame 600, which prevents the light leaks on the optical fiber lighting device 10.

As shown in FIG. 1, the entrance 510 of the optical fiber 500 faces the top surface 320 of the phosphor element 300, so as to receive the most part of first exciting light L1, second exciting light L2 and emission light L3. In present embodiment, the cross section area of the optical fiber 500 is substantial equal to the area of phosphor element 300, but is not limited thereto. In some embodiments, the area of phosphor element 300 can be larger or smaller than the cross section area of the optical fiber 500.

In present embodiment, the phosphor element 300 is excited by two different light sources from different directions, so the lighting efficiency and the luminous flux (lm) of the phosphor element 300 are improved. Therefore, the lighting module of the optical fiber lighting device 10 has higher luminous flux (lm), and the optical fiber lighting device 10 can provide brighter illumination (lx) light.

Second Embodiment

Figure 2:
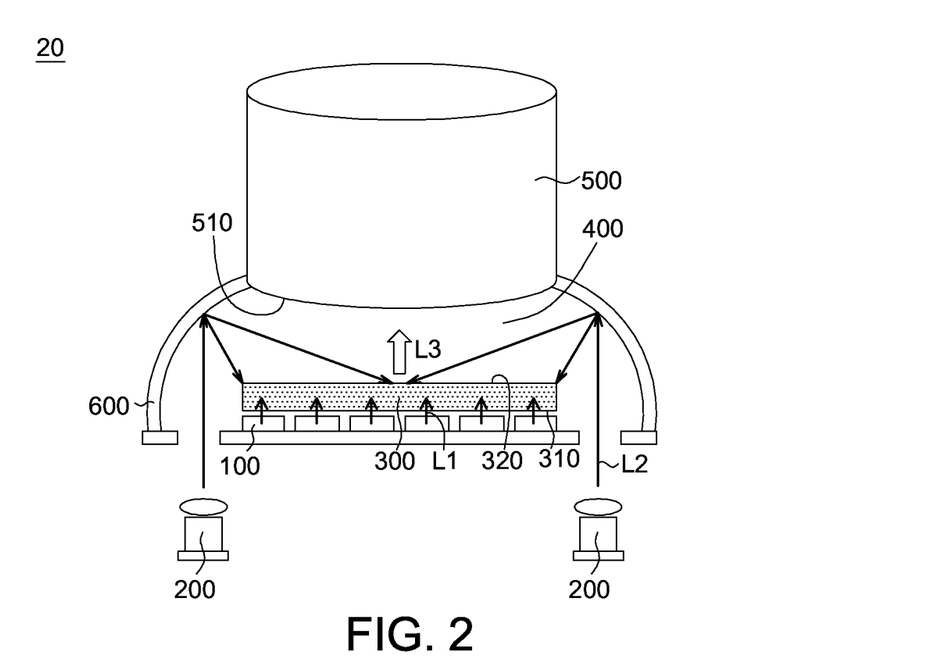
FIG. 2 shows an optical fiber lighting device according to a second embodiment.

Referring to FIG. 2, an optical fiber lighting device 20 according to a second embodiment is disclosed. The optical fiber lighting device 20 is similar to optical fiber lighting device 10 in FIG. 1, so the similarities shall be omitted herein. A difference of the second embodiment from the first embodiment is that, the first light source 100 and the second light source 200 are disposed on the same side of the phosphor element 300.

As shown in FIG. 2, the first light source 100 and the second light source 200 are disposed below the phosphor element 300. The first light source 100 is attached to the phosphor element 300, and the second light source 200 surrounds the phosphor element 300. It is note that the numbers of the second light source 200 are not limited to two LD units in this embodiment. In some embodiments, the second light source 200 could be only one LD unit or more than 3 LD units.

Moreover, the frame 600 is used for reflecting mask in FIG. 2, wherein the second exciting light L2 from the second light sources 200 are reflected at the frame 600 and then being guided to the top surface 320 of the phosphor element 300. That is, even if the first light sources 100 and the second light sources 200 are disposed at the same side, the first exciting light L1 and the second exciting light L2 still input to the phosphor element 300 through different directions of incidence, wherein the first exciting light L1 inputs the phosphor element 300 through its bottom surface 310, and the second exciting light L2 inputs the phosphor element 300 through its top surface 320. In addition to reflecting the second exciting light L2, the frame 600 keeps the function of defining the mixing chamber 400 and preventing the light leaks.

Third Embodiment

Figure 3:
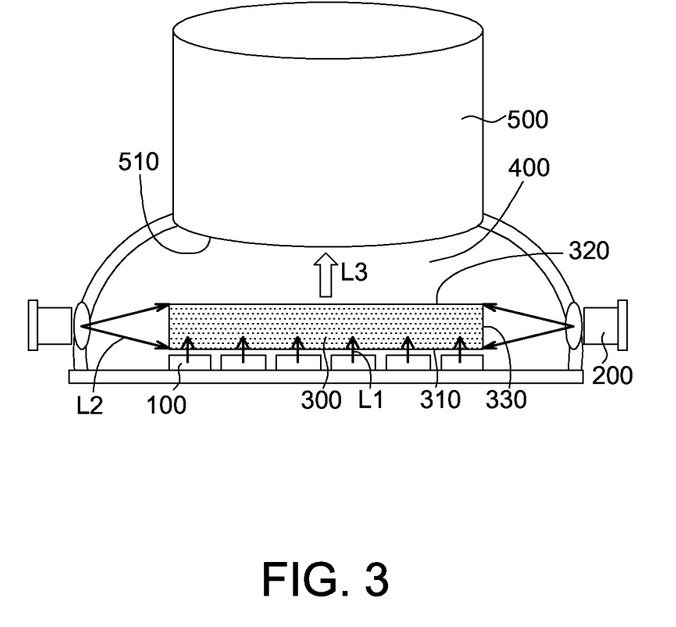
FIG. 3 shows an optical fiber lighting device according to a third embodiment.

Referring to FIG. 3, an optical fiber lighting device 30 according to a third embodiment is disclosed. The optical fiber lighting device 30 is similar to optical fiber lighting device 10 in FIG. 1, so the similarities shall be omitted herein. A difference of the third embodiment from the first embodiment is that, the second light sources 200 are disposed on the lateral side of the phosphor element 300.

As shown in FIG. 3, the second light source 200 (two LD units) are parallelly disposed at two different lateral sides of the phosphor element 300.

The first exciting light L1 inputs the phosphor element 300 through the bottom surface 310, and the second exciting light L2 inputs the phosphor element 300 through the lateral surface 330 being adjoining to and perpendicular to the bottom surface 310. Thus, the first exciting light L1 and the second exciting light L2 still input to the phosphor element 300 through different directions of incidence, so as to increase the irradiated area of the phosphor element 300.

It is noted that the number of the second light source 200 are not limited to two LD units. In other embodiment, the second light source 200 could be only one LD unit or more than 3 LD units.

Fourth Embodiment

Figure 4:
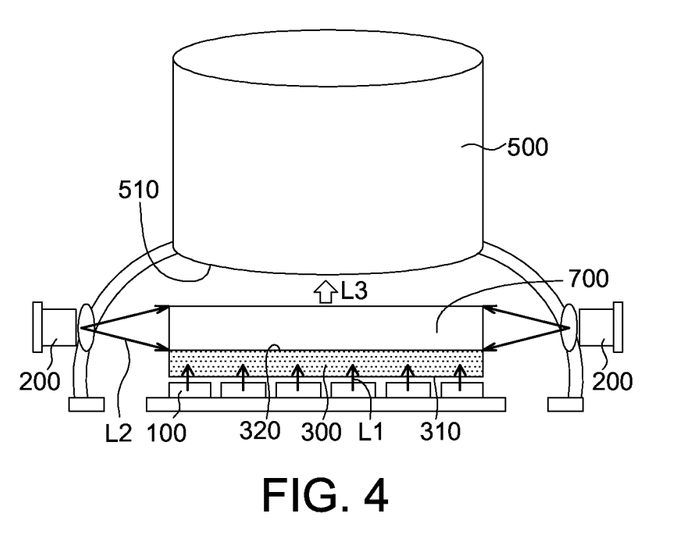
FIG. 4 shows an optical fiber lighting device according to a fourth embodiment.

Referring to FIG. 4, an optical fiber lighting device 40 according to a fourth embodiment is disclosed. The optical fiber lighting device 40 is similar to optical fiber lighting device 10 in FIG. 1, so the similarities shall be omitted herein. A difference of the fourth embodiment from the first embodiment is that, the optical fiber light device 40 in fourth embodiment further comprises a light guide plate 700.

As shown in FIG. 4, the light guide plate 700 is disposed above and attached the phosphor element 300, and the second light source 200 (two LD units) are parallelly disposed at two different lateral sides of the light guide plate 700. The second exciting light L2 is first passed through the light guide plate 700, being transmitted through the light guide plate 700 by means of total internal reflection, and then being transported to the top surface 320 of the phosphor element 300. That is, the light guide plate 700 distributes the second exciting light L2 to the phosphor element 300, so as to increase the irradiated area of the phosphor element 300.

It is noted that the first exciting light L1 and the second exciting light L2 still input to the phosphor element 300 through different directions of incidence, and the number of the second light source 200 are not limited to two LD units.

Fifth Embodiment

Figure 5:
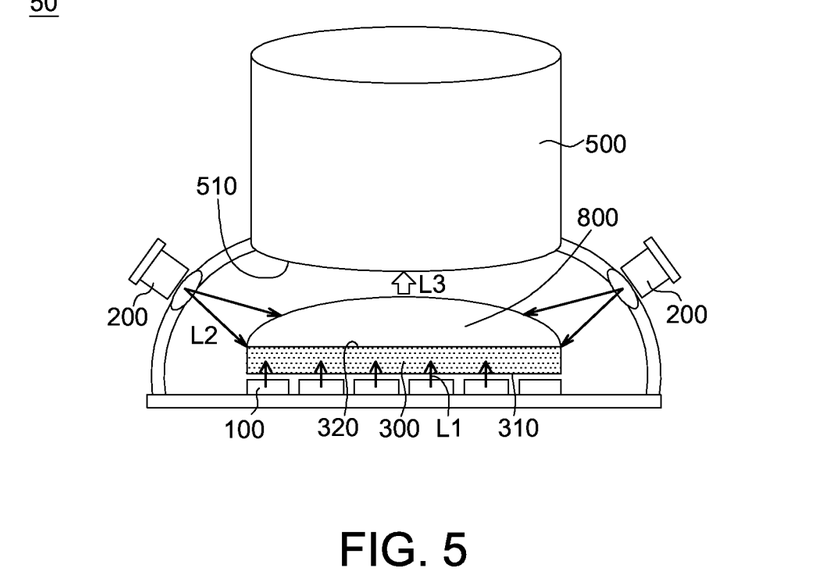
FIG. 5 shows an optical fiber lighting device according to a fifth embodiment.

Referring to FIG. 5, an optical fiber lighting device 50 according to a fifth embodiment is disclosed. The optical fiber lighting device 50 is similar to optical fiber lighting device 10 in FIG. 1, so the similarities shall be omitted herein. A difference of the fifth embodiment from the first embodiment is that, the optical fiber light device 50 in the fifth embodiment further comprises a lens 800.

As shown in FIG. 5, lens 800 is disposed above and attached the phosphor element 300. Lens 800 guides the second exciting light L2 into the phosphor element 300, so as to increase the irradiated area of the phosphor element 300.

In present embodiment, the second light source 200 and the first light source 100 are disposed at opposite sides of the phosphor element 300. In some embodiment, the second light source 200 and the first light source 100 can be disposed at the same side of the phosphor element 300. That is, the arrangement of second light source 200 in the second embodiment (FIG. 2) and lens 800 in present embodiment can be combined, and the disclosure is not limited to single embodiment.

As described above, the first exciting light L1 and the second exciting L2 inputs the phosphor element 300 through different directions of incidence. Thus, the irradiated area of the phosphor element 300 by the first exciting light L1 and the second exciting light L2 are different. By adjusting the irradiated area by different exciting lights L1, L2 (called "beam pattern" herein), the illumination of the emission light L3 can be improved. FIGS. 6A to 6D shown different beam patterns according to the embodiments.

Figure 6A:
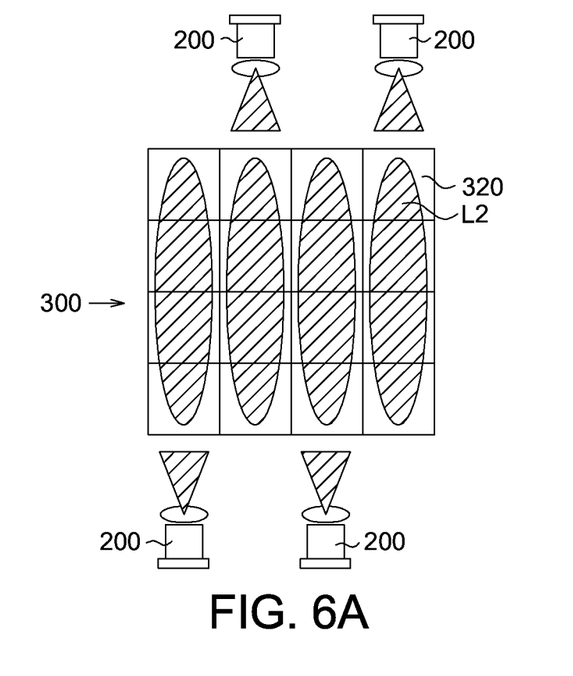
FIGS. 6A-6D show different beam patterns of the lighting module according to embodiments.

FIG. 6A is top view of the phosphor element 300 according to an embodiment, which shows the beam pattern of second exciting light L2. The first light source (not shown) is disposed below and attached the phosphor element 300, so the first exciting light (not shown) is evenly distributed to the bottom surface of phosphor element 300. The second light source 200, such as LD unit, has lower divergence angle (±2° for example) than that of the first light source, so the second exciting light L2 has narrow irradiated area. The beam pattern of second exciting light L2 is evenly distributed to the top surface 320 of the phosphor element 300. Thus, much more phosphors can be excited, and the illumination of the emission light L3 can be improved.

Figure 6B:
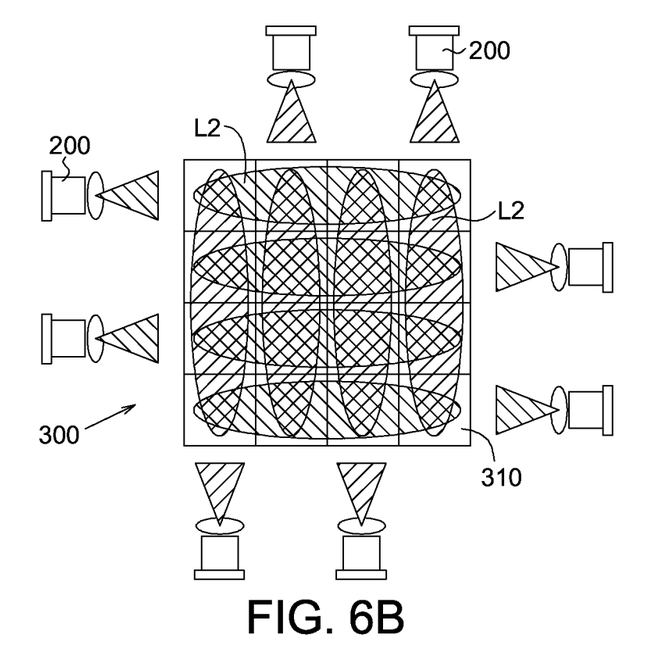

In FIG. 6A, the second light source 200 includes 4 LD units, and the beam pattern of the second exciting light L2 is evenly distributed. It is noted that the number of the LD units is not limited thereto. In other embodiment, second light source 200 includes 8 LD units and the light emitting from each LD unit may overlap. That is, beam patterns of different LD units may overlap to each other, as shown in FIG. 6B.

Figure 6C:
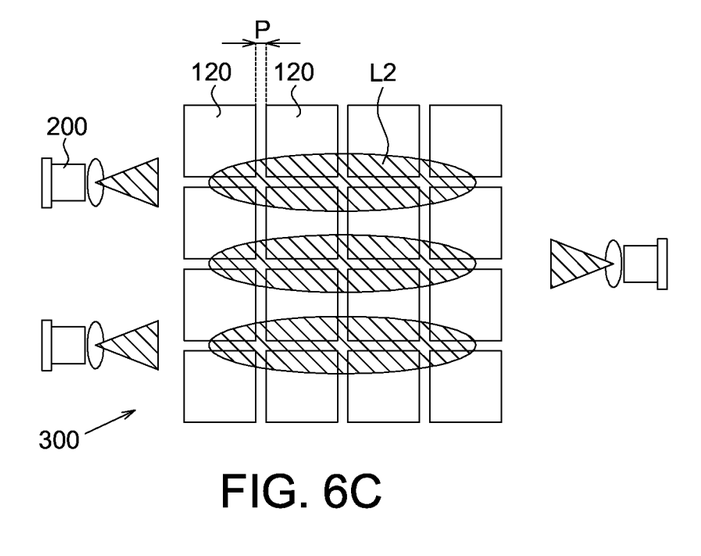

In FIG. 6C, the first light source 100 is a plurality of LEDs. The 16 LEDs 120 form a 4*4 LED array, and the two adjacent LEDs is spaced apart at pitch P. In this embodiment, the beam pattern of the second exciting light L2 is correspondingly distributed to pitch P. That is, phosphors inside phosphor element 300 and being located correspondingly to pitch P, which was hard to receive the first exciting light L1 from LED 120, can be excited and emit light, thereby illumination of the emission light L3 can be improved.

Figure 6D:
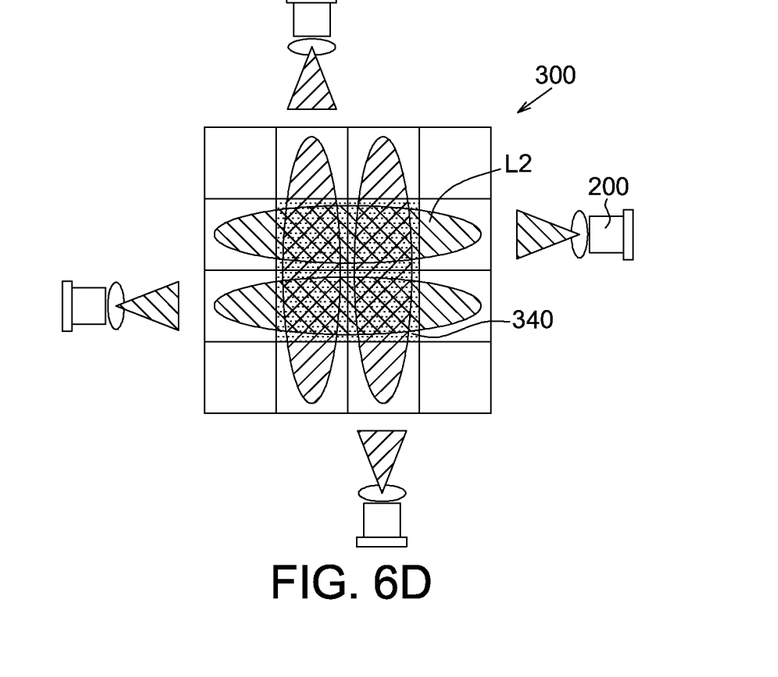

In FIG. 6D, phosphors in the phosphor element 300 are not evenly distributed. Since optical fiber is easily to receive the emission light from the center region 340 of the phosphor element 300, so phosphors thickness in the center region 340 of the phosphor element 300 are designed to higher than that in the peripheral region of the phosphor element 300. Thus, the beam pattern of second exciting light L2 is mainly distributed in the center region 340 of the phosphor element 300 in order to excite more phosphors, thereby illumination of the emission light L3 can be improved.

Figure 7A:
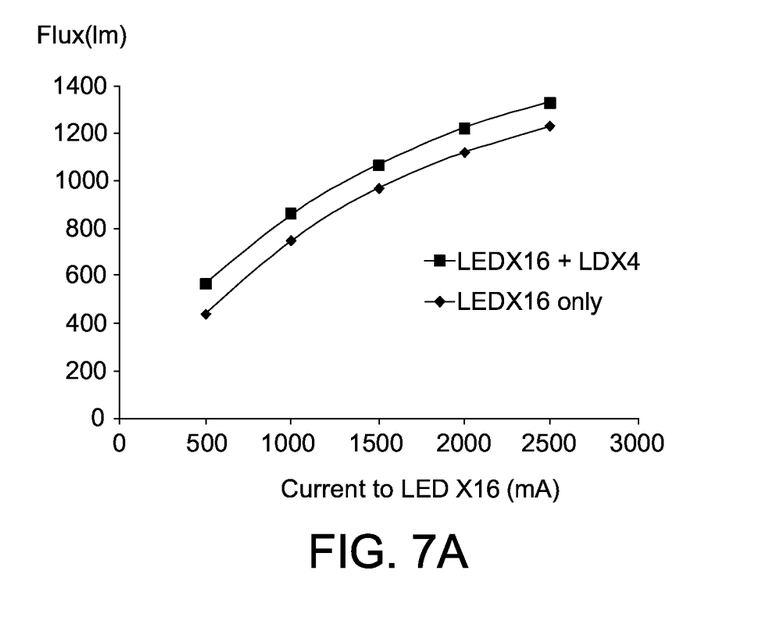
FIGS. 7A-7B are graphs of flux of lighting module versus current of LED, illustrating the lighting performance for lighting module with different light sources.
Figure 7B:
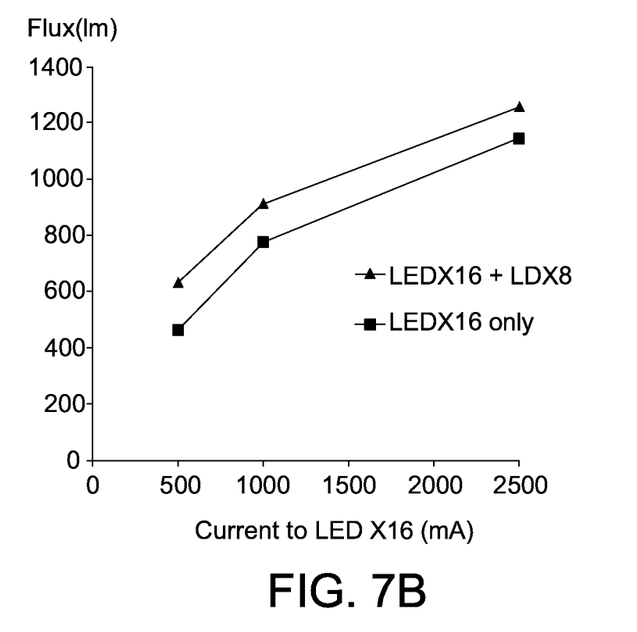

FIGS. 7A and 7B show the performance of the dual light source lighting module according to the embodiment, wherein FIG. 7A is a graph of flux verses current to LED for the dual light source (16 LEDs array+4 LDs) and for the single source (16 LEDs array) lighting module; FIG. 7B is a graph of flux verses current to LED for the dual light source (16 LEDs array+8 LDs) and for the single source (16 LEDs array) lighting module. The dual light source and the single light source lighting modules use the same phosphor element, and the LD and LED of the dual light source excite the same phosphor element.

Please referring to FIG. 7A, the 16 LEDs array provides about 1250 lm at current 2500 mA, and the 4 LDs produce about extra 100 lm from the same phosphor element. It proves that setting the extra second light source could excite more phosphor than setting the single light source. In FIG. 7B, the 8 LDs produce about extra 150 lm from the phosphor element excited by the 16 LEDs array. It should be realizes that the above experimental data are embodiment, and the present disclosures are not limited thereto.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A lighting module, comprising:
    a first light source for emitting a first exciting light;
    a second light source for emitting a second exciting light; and
    a phosphor element for converting the first exciting light and the second exciting light to an emission light,
    wherein the first exciting light and the second exciting light are input to the phosphor element in different directions of incidence;
    wherein the phosphor element has a bottom surface and a top surface opposite to the bottom surface;
    wherein the first exciting light is input to the phosphor element through the bottom surface, and the second exciting light is input to the phosphor element through the top surface.

2. The lighting module according to claim 1, further comprising:
    a reflecting mask for reflecting the second exciting light to the top surface of the phosphor element.

3. The lighting module according to claim 1, further comprising:
    a light guide plate for guiding the second exciting light to the top surface of the phosphor element.

4. The lighting module according to claim 1, further comprising:
    an optical fiber for receiving the first exciting light, the second exciting light and the emission light, wherein the optical fiber is disposed above the top surface of the phosphor element.

5. The lighting module according to claim 4, wherein a cross section area of the optical fiber is substantial equal to the area of the phosphor element.

6. The lighting module according to claim 4, further comprising:
    a lens for guiding the second exciting light to the top surface of the phosphor element and the emission light to the optical fiber.

7. The lighting module according to claim 1, wherein a divergent angle of the first light source is larger than that of the second light source.

8. The lighting module according to claim 7, wherein the first light source is a plurality of LEDs, the second light source is at least one LD, and the bottom surface of the phosphor element is attached to the LEDs.

9. The lighting module according to claim 8, wherein a beam pattern of the second exciting light is corresponding to a pitch between the LEDs.

10. The lighting module according to claim 8, wherein the second light source comprises a plurality of LDs, and beam patterns of different LDs are overlapped to each other.

11. The lighting module according to claim 1, wherein a beam pattern of the first exciting light is different from that of the second exciting light.

12. The lighting module according to claim 11, wherein a phosphors thickness in the phosphor element is not evenly distributed, the beam pattern of the first exciting light is evenly distributed over the whole phosphor element, and the beam pattern of the second exciting light is distributed over a portion of the phosphor element having higher phosphors thickness.

13. The lighting module according to claim 11, wherein the beam pattern of the second exciting light overlaps that of the first exciting light.

14. An optical fiber lighting device, comprising:
a first light source for emitting a first exciting light;
a second light source for emitting a second exciting light;
a phosphor element for converting the first exciting light and the second exciting light to an emission light, wherein the first exciting light and the second exciting light are input to the phosphor element in different directions of incidence;
an optical fiber for receiving the first exciting light, the second exciting light and the emission light, and the optical fiber is disposed above the phosphor element; and
a mixing chamber for mixing and guiding the first exciting light, the second exciting light and the emission light, and the mixing chamber is disposed between the optical fiber and the phosphor element.

15. A lighting module, comprising:
a first light source for emitting a first exciting light;
a second light source for emitting a second exciting light; and
a phosphor element for converting the first exciting light and the second exciting light to an emission light,
wherein the first exciting light and the second exciting light are input to the phosphor element in different directions of incidence,
wherein the phosphor element has a bottom surface and a lateral surface adjoining the bottom surface, and
wherein the first exciting light is input to the phosphor element through the bottom surface, and the second exciting light is input to the phosphor element through the lateral surface.

* * * * *